(12) United States Patent
Dehmlow et al.

(10) Patent No.: US 7,989,657 B2
(45) Date of Patent: Aug. 2, 2011

(54) ANTHRANILIC ACID DERIVATIVES

(75) Inventors: Henrietta Dehmlow, Grenzach-Wyhlen (DE); Uwe Grether, Efringen-Kirchen (DE); Nicole A Kratochwil, Sool (CH); Robert Narquizian, St. Louis (FR); Constantinos Panousis, Bottmingen (CH); Jens-Uwe Peters, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/477,525

(22) Filed: Jun. 3, 2009

(65) Prior Publication Data

US 2009/0247637 A1   Oct. 1, 2009

Related U.S. Application Data

(63) Continuation of application No. 11/451,005, filed on Jun. 12, 2006, now abandoned.

(30) Foreign Application Priority Data

Jun. 14, 2005 (EP) .................................. 05105176

(51) Int. Cl.
C07C 235/00 (2006.01)
C07C 229/56 (2006.01)
(52) U.S. Cl. ......................................... 562/455; 562/433
(58) Field of Classification Search .................... None
See application file for complete search history.

(56) References Cited

U.S. PATENT DOCUMENTS

2005/0113450 A1* 5/2005 Thorarensen et al. ........ 514/562

FOREIGN PATENT DOCUMENTS

| JP | 02 218654 | 8/1990 |
|---|---|---|
| WO | 00/05198 | 3/2000 |
| WO | 01/60354 | 8/2001 |
| WO | WO 2004/018414 | 3/2004 |
| WO | 2005/016867 | 2/2005 |
| WO | WO 2005/016870 | 2/2005 |
| WO | 2005/077950 | 8/2005 |
| WO | 2006/083491 | 8/2006 |
| WO | 2006/085108 | 8/2006 |

OTHER PUBLICATIONS

Nie et al. J. Med. Chem. 2005, 48,15-96-1609.*
Jin et al Arterioscler. Thromb. Vasc. Biol. 1997, 17, 2020-2028.
Grundy et al Arch Intern Med 2002, 162, 1568-76.
Wise et. al. J Biol Chem. 2003, 278 (11) 9869-9874.
Soga et al Biochem Biophys Res Commun 2003 303 (1) 364-369.
Tunaru et al Nature Medicine 2003, (3) 352-255.
Z.J. Song et al., Organic Letters, 4, 1623; 2002.
R.C. Larock et al., Organic Letters, 6, 99; 2004.
J.F. Hartwig et al., J. Am. Chem. Soc., 121, 3224; 1999.
Hasegawam M. et al, J Med. Chem., vol. 40 (1997) pp. 395-407, XP001015552.
English Translation of Japanese Office Action for Corres. Appl. 2008-516275 dated Dec. 21, 2010.

* cited by examiner

*Primary Examiner* — Daniel Sullivan
*Assistant Examiner* — Yevegeny Valenrod
(74) *Attorney, Agent, or Firm* — George W. Johnston; Dennis P. Tramaloni; Samuel H. Megerditchain

(57) ABSTRACT

The invention is concerned with novel anthranilic acid derivatives of formula (I)

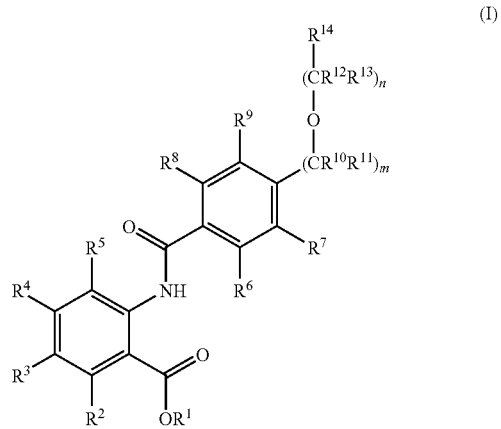

wherein $R^1$ to $R^{14}$, m and n are as defined in the description and in the claims, as well as physiologically acceptable salts and esters thereof. These compounds are HM74A agonists and can be used as medicaments.

2 Claims, No Drawings

ANTHRANILIC ACID DERIVATIVES

PRIORITY TO RELATED APPLICATIONS

This application is a continuation, of U.S. application Ser. No. 11/451,005, filed Jun. 12, 2006, now Pending, which claims the benefit of European Application No. 05105176.1, filed Jun. 14, 2005. The entire contents of the above-identified applications are hereby incorporated by reference in its entirety.

FIELD OF THE INVENTION

The invention is directed to novel anthranilic acid derivatives of the formula (I)

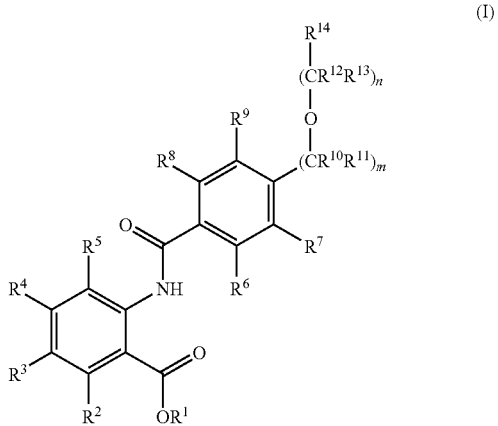

and pharmaceutically acceptable salts and pharmaceutically acceptable esters thereof.

Further, the invention is directed to a process for the manufacture of the above compounds, pharmaceutical preparations which contain such compounds as well as the use of these compounds for the production of pharmaceutical preparations.

All documents cited or relied upon below are expressly incorporated herein by reference.

BACKGROUND

Coronary heart disease (CHD) remains the leading cause of death in Western countries. In the United States 13.2 million or 4.85% of the population is affected, with 1.2 million new or recurrent attacks and around 500 thousand deaths per year (American Heart Association, Statistics for 2001). The disease is influenced by several well-established risk factors, such as age, sex, blood lipids, blood pressure, smoking, diabetes, and body mass index (BMI) as an indicator of overweight and obesity. The National Cholesterol Education Program (NCEP) Adult Treatment Panel III defines elevated plasma levels of low density lipoprotein (LDL) cholesterol (LDL-C$\geq$160 mg/dL), and low levels of high density lipoprotein (HDL) cholesterol (HDL-C$\leq$40 mg/dL) as independent risk factors for CHD. Many prospective epidemiological studies have indicated that a decreased HDL-C level is a significant independent risk factor for heart disease, while increased HDL-C levels$\geq$60 mg/dL ($\geq$1.55 mmol) have a protective role against CHD.

Nicotinic acid (Niacin), a vitamin of the B complex, is used for almost 40 years as a lipid-lowering drug with a favorable profile for all lipoprotein classes. Numerous clinical studies have shown the beneficial effects of niacin, demonstrating a reduction of coronary artery disease and overall mortality. Niacin is the most potent agent currently available to raise HDL. It has been proposed than niacin's main mode of action is through inhibition of lipolysis in the adipose tissue having as a result the reduction of free fatty acids (FFA) in plasma and liver and consequently the decreased production of very low density lipoproteins (VLDL), accounting for the reduction of total cholesterol (TC), triglycerides (TGs), and LDL-C. Due to the decreased TG rich lipoproteins levels, less modification of HDL particles occurs upon the action of cholesteryl ester transfer protein (CETP), resulting in a decreased catabolism of HDL. A direct inhibition of lipoprotein AI-HDL (LPAI-HDL) particle uptake by the liver has been also proposed, accounting for the overall HDL raising properties of niacin (Jin et al Arterioscler. Thromb. Vasc. Biol. 1997, 17, 2020-2028).

Niacin also has anti-diabetic, anti-thrombotic and anti-inflammatory properties that contribute to the overall cardio-protective effects. Through a variety of mechanisms niacin reduces thrombosis, such as the reduction of lipoprotein (a) (Lp(a)) which is a potent inhibitor of fibrinolytic activity, and it is the only currently approved drug that effectively reduces the serum levels of Lp(a) (Carlson et al J Intern Med 1989, 17, 2020-8). Inflammation is a critical component of atherosclerosis, leading to recruitment of macrophages which both promote plaque development and decrease plaque stability thus increasing cardiovascular risk. Niacin has been suggested to have anti-inflammatory properties, such as the reduction of C-reactive protein (CRP) levels (Grundy et al Arch Intern Med 2002, 162, 1568-76). Several prospective studies have established a strong and direct correlation between cardiovascular risk and CRP levels, a measure of vascular inflammation. Extensive use of niacin has been hampered due to side effects, mainly intense cutaneous flushing.

Recently HM74A/HM74, a G-protein coupled receptor (GPCR), was identified as a receptor for niacin and proposed as the mediator of the niacin effects (Wise et. al. J Biol. Chem. 2003, 278 (11) 9869-9874 and Soga et al Biochem Biophys Res Commun 2003 303 (1) 364-369). In support, deletion of the PUMA-G (HM74A orthologue) in mice abrogated the niacin effects on reduction of plasma free fatty acids and triglycerides (Tunaru et al Nature Medicine 2003, (3) 352-255).

Thus, a need exists for compounds selective for HM74A for the treatment and/or prevention of diseases modulated by HM74A agonists.

SUMMARY OF THE INVENTION

In one embodiment of the present invention, provided is a compound of formula (I):

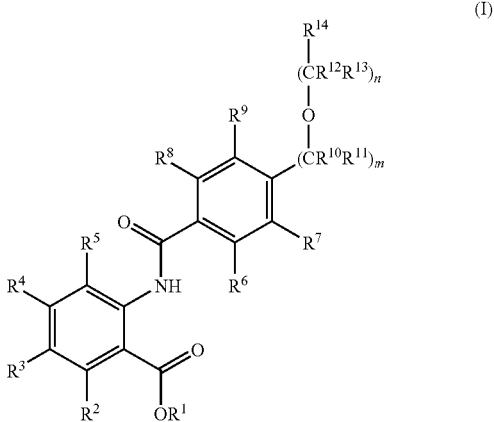

wherein
R$^1$ is hydrogen or lower-alkyl;
R$^2$, R$^3$, R$^4$ and R$^5$, independently from each other, are hydrogen, halogen, lower-alkyl or fluoro-lower-alkyl, with the proviso that R$^4$ is not bromine;
R$^6$, R$^7$, R$^8$ and R$^9$, independently from each other, are hydrogen, lower-alkyl, lower-alkoxy, cycloalkyl, halogen, lower-alkoxy-lower-alkyl, fluoro-lower-alkyl, fluoro-lower-alkoxy, lower alkenyl, lower alkinyl or cyano;
R$^{10}$, R$^{11}$, R$^{12}$ and R$^{13}$ independently from each other are hydrogen, lower-alkyl or fluoro-lower-alkyl, or R$^{10}$ and R$^{11}$ are bound together to form a cycloalkyl together with the carbon atom to which they are attached and —R$^{10}$—R$^{11}$— is —(CH$_2$)$_{2-6}$—, or R$^{12}$ and R$^{13}$ are bound together to form a cycloalkyl together with the carbon atom to which they are attached and —R$^{12}$—R$^{13}$— is —(CH$_2$)$_{2-6}$—;
R$^{14}$ is phenyl or heteroaryl, which phenyl or heteroaryl is optionally substituted with 1 to 3 substituents selected from the group consisting of halogen, lower-alkyl, hydroxy-lower-alkyl, lower-alkoxy, fluoro-lower-alkoxy, carboxy, carboxy-lower-alkyl, lower-alkoxy-carbonyl, lower-alkoxy-carbonyl-lower-alkyl, R$^{15}$R$^{16}$NC(O), R$^{15}$R$^{16}$NC(O)-lower-alkyl, fluoro-lower-alkyl, R$^{15}$R$^{16}$N-lower-alkyl, R$^{15}$R$^{16}$N, lower-alkyl-SO$_2$, lower-alkyl-SO$_2$O, lower-alkyl-SO$_2$—NR$^{15}$, R$^{15}$R$^{16}$NSO$_2$, cyano, heteroaryl, cycloalkyl, lower-alkoxy-lower-alkyl, lower-alkenyl, lower-alkinyl, fluoro-lower-alkoxy-lower-alkyl, cyano-lower-alkyl;
R$^{15}$ and R$^{16}$ independently from each other are hydrogen or lower-alkyl;
m is 0 or 1;
n is 0 or 1;
and pharmaceutically acceptable salts and pharmaceutically acceptable esters thereof;
with the proviso that the compound of formula (I) is not selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester.
In another embodiment of the present invention, provided is a process for the manufacture of compounds of formula (I), which process comprises reacting a compound of formula (II)

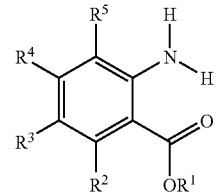

with a compound of formula (III),

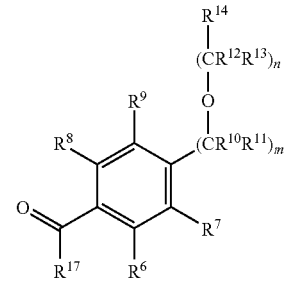

wherein R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, m and n are as defined above and R$^{17}$ is OH, Cl, Br, or a carboxylic acid moiety to form an anhydride;
or
hydrolysis of a compound of formula (Ia)

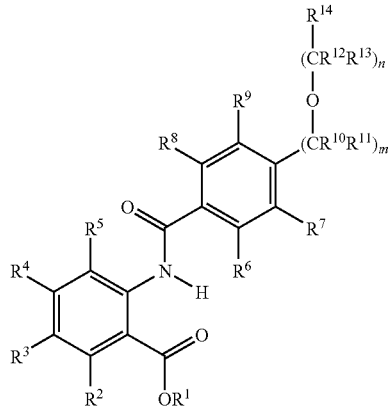

wherein R$^2$, R$^3$, R$^4$, R$^5$, R$^6$, R$^7$, R$^8$, R$^9$, R$^{10}$, R$^{11}$, R$^{12}$, R$^{13}$, R$^{14}$, m and n are as defined above and R$^1$ is lower-alkyl.
In a further embodiment of the present invention, provided is a pharmaceutical composition, comprising a therapeutically effective amount of a compound according to formula (I) or a compound selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester, 2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester,
and a pharmaceutically acceptable carrier and/or adjuvant.

In a yet another embodiment of the present invention, provided is a method for the treatment and/or prevention of diseases which are modulated by HM74A agonists, comprising the step of administering a therapeutically effective amount of a compound according to formula (I) or a compound selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester, to a human being or animal in need thereof.

DETAILED DESCRIPTION

The novel compounds of the present invention exceed the compounds known in the art, inasmuch as they bind to and activate HM74A. The compounds of the present invention are selective for HM74A by which is meant that they show greater affinity for HM74A than for HM74. The compounds of the present invention are expected to have an enhanced therapeutic potential and exhibit reduced side effects compared to nicotinic acid. The compounds of the present invention can be used as medicaments for the treatment and/or prevention of diseases which are modulated by HM74A agonists. Examples of such diseases are increased lipid and cholesterol levels, particularly dyslipidemia, low HDL-cholesterol, atherosclerotic diseases, hypertriglyceridemia, thrombosis, angina pectoris, peripheral vascular disease, stroke, diabetes, particularly non-insulin dependent diabetes mellitus, metabolic syndrome, Alzheimer's disease, Parkinson's disease, schizophrenia, sepsis, inflammatory diseases (such as e.g. colitis, pancreatitis, cholestasis/fibrosis of the liver, and diseases that have an inflammatory component such as e.g. Alzheimer's disease or impaired/improvable cognitive function).

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups can optionally be substituted, e.g. by hydroxy or cyano. Such substituted lower-alkyl-groups are referred to as "hydroxy-lower-alkyl" or "cyano-lower-alkyl". Unsubstituted lower-alkyl groups are preferred The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H-CF_2$.

The term "alkenyl", alone or in combination with other groups, stands for a straight-chain or branched hydrocarbon residue comprising an olefinic bond and up to 20, preferably up to 16 carbon atoms. The term "lower-alkenyl" refers to a straight-chain or branched hydrocarbon residue comprising an olefinic bond and up to 7, preferably up to 4 carbon atoms, such as e.g. 2-propenyl.

The term "alkinyl", alone or in combination with other groups, stands for a straight-chain or branched hydrocarbon residue comprising a triple bond and up to 20, preferably up to 16 carbon atoms. The term "lower-alkinyl" refers to a straight-chain or branched hydrocarbon residue comprising a triple bond and up to 7, preferably up to 4 carbon atoms, such as e.g. 2-propinyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, $-NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are e.g. CFH$_2$—O, CF$_2$H—O, CF$_3$—O, CF$_3$CH$_2$—O, CF$_3$(CH$_2$)$_2$—O, (CF$_3$)$_2$CH—O, and CF$_2$H—CF$_2$—O.

The term "aryl", alone or in combination, relates to the phenyl or naphthyl group, preferably the phenyl group, which can optionally be substituted by 1 to 5, preferably 1 to 3, substituents independently selected from the group consisting of halogen, lower-alkyl, hydroxy-lower-alkyl, lower-alkoxy, carboxy, carboxy-lower-alkyl, lower-alkoxy-carbonyl, lower-alkoxy-carbonyl-lower-alkyl, H$_2$NC(O), (H, lower-alkyl)NC(O), (lower-alkyl)$_2$NC(O), H$_2$NC(O)-lower-alkyl, (H, lower-alkyl)NC(O)-lower-alkyl, (lower-alkyl)$_2$NC(O)-lower-alkyl, fluoro-lower-alkyl, H$_2$N-lower-alkyl, (H, lower-alkyl)N-lower-alkyl, (lower-alkyl)$_2$N-lower-alkyl, lower-alkyl-SO$_2$, lower-alkyl-SO$_2$O, lower-alkyl-SO$_2$—NH lower-alkyl-SO$_2$—N(lower-alkyl), H$_2$NSO$_2$, (H, lower-alkyl)NSO$_2$, (lower-alkyl)$_2$NSO$_2$, cyano, heteroaryl, cycloalkyl, lower-alkoxy-lower-alkyl, lower-alkenyl, lower-alkinyl, fluoro-lower-alkoxy-lower-alkyl, cyano-lower-alkyl. Other possible substituents are e.g. hydroxy, amino, NO$_2$, dioxo-lower-alkylene (forming e.g. a benzodioxyl group), lower-alkylcarbonyl, lower-alkylcarbonyloxy, lower-alkylcarbonyl-NH, cycloalkyl, phenyl and phenyloxy. Preferred substituents are halogen, lower-alkyl, fluoro-lower-alkyl, lower-alkoxy and fluoro-lower-alkoxy. Furthermore, aryl groups can be substituted as described in the description below.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl and quinolinyl. Preferred heteroaryl groups are pyridinyl and quinolinyl. A heteroaryl group may be unsubstituted or optionally have a substitution pattern as described earlier in connection with the term "aryl". Furthermore, a heteroaryl group may be substituted as described in the specification below and in the claims.

The term "protecting group" (PG) refers to groups such as e.g. acyl, alkoxycarbonyl, aryloxycarbonyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Compounds of formula (I) in which a COOH group is present can form salts with bases. Examples of such salts are alkaline, earth-alkaline and ammonium salts such as e.g. Na-, K-, Ca-, Mg- and trimethylammonium-salt. The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

In detail, the present invention relates to compounds of formula (I)

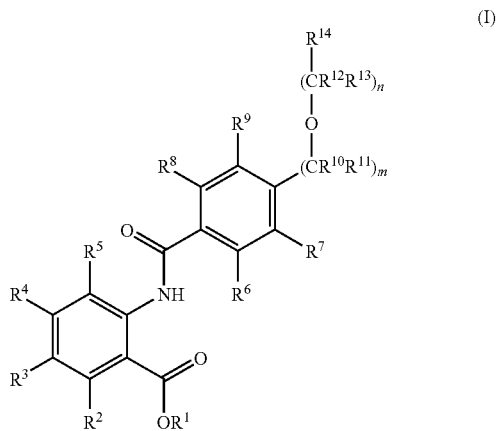

wherein
R$^1$ is hydrogen or lower-alkyl;
R$^2$, R$^3$, R$^4$ and R$^5$, independently from each other, are hydrogen, halogen, lower-alkyl or fluoro-lower-alkyl, with the proviso that R$^4$ is not bromine;
R$^6$, R$^7$, R$^8$ and R$^9$, independently from each other, are hydrogen, lower-alkyl, lower-alkoxy, cycloalkyl, halogen, lower-alkoxy-lower-alkyl, fluoro-lower-alkyl, fluoro-lower-alkoxy, lower alkenyl, lower alkinyl or cyano;
R$^{10}$, R$^{11}$, R$^{12}$ and R$^{13}$ independently from each other are hydrogen, lower-alkyl or fluoro-lower-alkyl, or R$^{10}$ and R$^{11}$ are bound together to form a cycloalkyl together with the carbon atom to which they are attached and —R$^{10}$—R$^{11}$— is —(CH$_2$)$_{2-6}$—, or R$^{12}$ and R$^{13}$ are bound together to form a cycloalkyl together with the carbon atom to which they are attached and —R$^{12}$—R$^{13}$— is —(CH$_2$)$_{2-6}$—;
R$^{14}$ is phenyl or heteroaryl, which phenyl or heteroaryl is optionally substituted with 1 to 3 substituents selected from the group consisting of halogen, lower-alkyl, hydroxy-lower-alkyl, lower-alkoxy, fluoro-lower-alkoxy, carboxy, carboxy-lower-alkyl, lower-alkoxy-carbonyl, lower-alkoxy-carbonyl-lower-alkyl, R$^{15}$R$^{16}$NC(O), R$^{15}$R$^{16}$NC(O)-lower-alkyl, fluoro-lower-alkyl, R$^{15}$R$^{16}$N-lower-alkyl, R$^{15}$R$^{16}$N, lower-alkyl-SO$_2$, lower-alkyl-SO$_2$O, lower-alkyl-SO$_2$—NR$^{15}$, R$^{15}$R$^{16}$NSO$_2$, cyano, heteroaryl, cycloalkyl, lower-alkoxy-lower-alkyl, lower-alkenyl, lower-alkinyl, fluoro-lower-alkoxy-lower-alkyl, cyano-lower-alkyl;
R$^{15}$ and R$^{16}$ independently from each other are hydrogen or lower-alkyl;
m is 0 or 1;
n is 0 or 1;
and pharmaceutically acceptable salts and pharmaceutically acceptable esters thereof;

with the proviso that the compound of formula (I) is not selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, diastereomeric mixture or as optically pure compounds.

Preferred compounds of formula (I) as described above are those, wherein $R^1$ is hydrogen. In compounds wherein $R^1$ is lower-alkyl, $R^1$ preferably is $C_{2-7}$-alkyl. Other preferred compounds of formula (I) as described above are those wherein $R^2$, $R^3$, $R^4$ and $R^5$, independently from each other, are hydrogen, halogen or fluoro-lower-alkyl, with the proviso that $R^4$ is not bromine. Preferably $R^2$, $R^3$, $R^4$ and $R^5$, independently from each other, are hydrogen or halogen, with the proviso that $R^4$ is not bromine. Preferably, $R^2$ is hydrogen or fluorine. Other preferred compounds are those, wherein $R^3$ is hydrogen. Still other preferred compounds are those, wherein $R^4$ is hydrogen or fluorine. Compounds, wherein $R^5$ is hydrogen are also preferred.

Another preferred embodiment of the present invention relates to compounds of formula (I) as defined above, wherein $R^6$, $R^7$, $R^8$ and $R^9$, independently from each other, are hydrogen, lower-alkyl or lower-alkoxy. In such compounds, $R^6$ preferably is hydrogen, methyl or methoxy. Other preferred compounds are those, wherein $R^7$ is hydrogen or methyl. Compounds wherein $R^8$ is hydrogen are also preferred. Further preferred compounds are those, wherein $R^9$ is hydrogen.

Another preferred embodiment of the present invention refers to compounds of formula (I) as described above, wherein $R^{14}$ is pyridinyl, quinolinyl or phenyl which is optionally substituted with 1 to 3 substituents selected from the group consisting of halogen, lower-alkyl, lower-alkoxy, lower-alkyl-SO$_2$, lower-alkoxy-carbonyl, cyano, fluoro-lower-alkyl, $R^{15}R^{16}NC(O)$ and triazolyl, wherein $R^{15}$ and $R^{16}$ independently from each other are hydrogen or lower-alkyl. Among these compounds, those are particularly preferred, wherein $R^{14}$ is phenyl, 2-methyl-phenyl, 2-fluoro-phenyl, 2-chloro-phenyl, 3-fluoro-phenyl, 3-methyl-phenyl, quinolin-8-yl, 4-[1,2,4]-triazol-1-yl-phenyl, 2,4-difluoro-phenyl, pyridin-2-yl or 2,5-difluoro-phenyl.

In other preferred compounds of the present invention m is 0. Compounds, wherein n is 0 or 1 and $R^{12}$ and $R^{13}$ are hydrogen are also preferred, particularly those, wherein n is 0.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of:
2-(4-Benzyloxy-benzoylamino)-benzoic acid,
2-[4-(4-Fluoro-phenoxy)-benzoylamino]-benzoic acid,
2-[4-(3,4-Dichloro-phenoxy)-benzoylamino]-benzoic acid,
2-(4-p-Tolyloxy-benzoylamino)-benzoic acid,
2-[4-(3-Methoxy-phenoxy)-benzoylamino]-benzoic acid,
2-(4-o-Tolyloxy-benzoylamino)-benzoic acid,
2-[4-(4-Methoxy-phenoxy)-benzoylamino]-benzoic acid,
2-[4-(4-Chloro-phenoxy)-benzoylamino]-benzoic acid,
2-[4-(3,4-Difluoro-phenoxy)-benzoylamino]-benzoic acid,
2-[4-(4-Methanesulfonyl-phenoxy)-benzoylamino]-benzoic acid,
2-{4-[4-Methoxycarbonyl)phenoxy]benzoyl}aminobenzoic acid,
2-[4-(3,5-Dichloro-phenoxy)-benzoylamino]-benzoic acid,
2-[4-(4-Cyano-phenoxy)-benzoylamino]-benzoic acid,
2-[4-(2-Fluoro-phenoxy)-benzoylamino]-benzoic acid,
2-[4-(2-Chloro-phenoxy)-benzoylamino]-benzoic acid,
2-[4-(3-Fluoro-phenoxy)-benzoylamino]-benzoic acid,
2-[4-(3-Chloro-phenoxy)-benzoylamino]-benzoic acid,
2-(4-m-Tolyloxy-benzoylamino)-benzoic acid,
2-[4-(Quinolin-8-yloxy)-benzoylamino]-benzoic acid,
2-[4-(4-Trifluoromethyl-phenoxy)-benzoylamino]-benzoic acid,
2-[4-(4-Carbamoyl-phenoxy)-benzoylamino]-benzoic acid,
2-[4-(4-Dimethylaminomethyl-phenoxy)-benzoylamino]-benzoic acid,
2-[4-(4-[1,2,4]Triazol-1-yl-phenoxy)-benzoylamino]-benzoic acid,
2-[4-(2,4-Difluoro-phenoxy)-benzoylamino]-benzoic acid,
2-[4-(Pyridin-2-yloxy)-benzoylamino]-benzoic acid,
2-[4-(Pyridin-3-yloxy)-benzoylamino]-benzoic acid,
2-[4-(3,4-Dimethyl-phenoxy)-benzoylamino]-benzoic acid,
2-[4-(2,3-Difluoro-phenoxy)-benzoylamino]-benzoic acid,
2-[4-(2,5-Difluoro-phenoxy)-benzoylamino]-benzoic acid,
2-(3-Methyl-4-phenoxy-benzoylamino)-benzoic acid,
2-(2-Methyl-4-phenoxy-benzoylamino)-benzoic acid,
2-(2-Methoxy-4-phenoxy-benzoylamino)-benzoic acid,
5-Fluoro-2-(4-phenoxy-benzoylamino)-benzoic acid,
4-Fluoro-2-(4-phenoxy-benzoylamino)-benzoic acid, and
2-Fluoro-6-(4-phenoxy-benzoylamino)-benzoic acid,
and pharmaceutically acceptable salts and esters thereof.

Particularly preferred compounds of formula (I) are those selected from the group consisting of
2-(4-o-Tolyloxy-benzoylamino)-benzoic acid,
2-[4-(2-Fluoro-phenoxy)-benzoylamino]-benzoic acid,
2-[4-(2-Chloro-phenoxy)-benzoylamino]-benzoic acid,
2-[4-(3-Fluoro-phenoxy)-benzoylamino]-benzoic acid,
2-(4-m-Tolyloxy-benzoylamino)-benzoic acid,
2-[4-(Quinolin-8-yloxy)-benzoylamino]-benzoic acid,
2-[4-(4-[1,2,4]Triazol-1-yl-phenoxy)-benzoylamino]-benzoic acid,
2-[4-(2,4-Difluoro-phenoxy)-benzoylamino]-benzoic acid,
2-[4-(Pyridin-2-yloxy)-benzoylamino]-benzoic acid,
2-[4-(2,5-Difluoro-phenoxy)-benzoylamino]-benzoic acid,
2-(3-Methyl-4-phenoxy-benzoylamino)-benzoic acid, 4-Fluoro-2-(4-phenoxy-benzoylamino)-benzoic acid, and 2-Fluoro-6-(4-phenoxy-benzoylamino)-benzoic acid and pharmaceutically acceptable salts and esters thereof.

Other preferred compounds as defined above are those selected from the group consisting of 2-[4-(3-Fluoro-phenoxy)-3-methyl-benzoylamino]-benzoic acid, 2-[4-(2-Fluoro-phenoxy)-3-methyl-benzoylamino]-benzoic acid, 2-[4-(2,4-Difluoro-phenoxy)-3-methyl-benzoylamino]-benzoic acid, 4-Chloro-5-fluoro-2-(4-phenoxy-benzoylamino)-benzoic acid, and 2-(4-Phenoxy-benzoylamino)-5-trifluoromethyl-benzoic acid, and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (II)

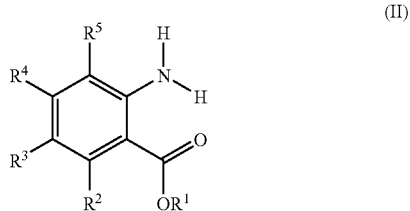

(II)

with a compound of formula (III), (III)

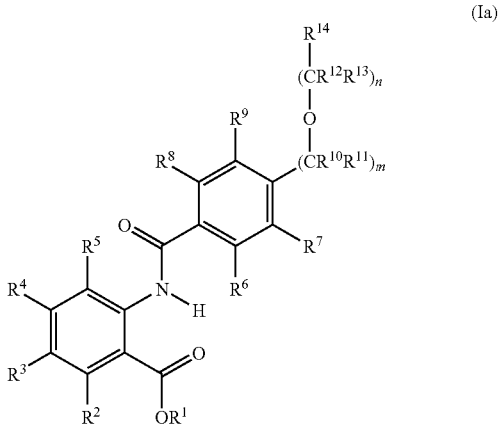

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, m and n are as defined above and $R^{17}$ is OH, Cl, Br, or a carboxylic acid moiety to form an anhydride;

or hydrolysis of a compound of formula (Ia)

(Ia)

wherein $R^2$, $R^3$, $R^4$, $R^5$, $R^6$, $R^7$, $R^8$, $R^9$, $R^{10}$, $R^{11}$, $R^{12}$, $R^{13}$, $R^{14}$, m and n are as defined above and $R^1$ is lower-alkyl.

If $R^{17}$ is a carboxylic acid moiety, it is preferably pivaloylic acid, p-nitrobenzoic acid, p-trifluoromethylbenzoic acid, 2,4,6-trichloro benzoic acid, acetic acid, trifluoroacetic acid, carbonic acid monoisobutyl ester, diphenyl phosphinic acid or benzene sulfonic acid to form an asymmetric anhydride, or it is the remainder of a second moiety of formula (III) bound via an oxygen atom to form a symmetric anhydride. Preferably, $R^{17}$ is Cl.

The reaction of a compound of formula (II) with a compound of formula (III) or the reaction of a compound of formula (Ia) can be performed under reaction conditions well known to the person skilled in the art. Such reactions can conveniently be carried out for amide bond formation (process a)) with compounds of formula (III) ($R^{17}$=Cl, Br) or with mixed or symmetric anhydrides (III), wherein $R^{17}$ is a carboxylic acid moiety such as e.g. pivaloylic acid, p-nitrobenzoic acid, p-trifluoromethylbenzoic acid, 2,4,6-trichloro benzoic acid, acetic acid, trifluoroacetic acid, carbonic acid monoisobutyl ester, diphenyl phosphinic acid or benzene sulfonic acid or the remainder of a second moiety of formula (III) bound via an oxygen atom to form a symmetric anhydride, in a solvent such as dichloromethane, in the presence of a base such as triethylamine, ethyl-diisopropyl-amine or N-ethylmorpholine at temperatures between 0° C. and ambient temperature, with compounds of formula (III) ($R^{17}$=OH) in the presence of N-(3-dimethylaminopropyl)-N'-ethyl-carbodiimide-hydrochloride or BOP (benzotriazol-1-yloxytris(dimethylamino)phosphonium hexafluorophosphate) in the presence of a base such as ethyl-diisopropyl-amine, triethylamine, N-methylmorpholine optionally in the presence of 4-dimethylamino-pyridine or HOBt (1-hydroxy-benzo-triazole) in solvents such as dichloromethane, DMF, DMA or dioxane at temperatures between 0° C. and ambient temperature or for process (b) by treatment with an alkali hydroxide like LiOH or NaOH in a polar solvent such as tetrahydrofuran, methanol, ethanol or water or mixtures thereof. If one of the starting materials II, III or Ia contains one or more functional groups which are not stable or are reactive under the reaction conditions, appropriate protecting groups (as described e.g. in "Protective Groups in Organic Chemistry" by T. W. Greene and P. G. M. Wutts, $2^{nd}$ Ed., 1991, Wiley N. Y.) can be introduced before the condensation step applying methods well known in the art. Such protecting groups can be removed at a later stage of the synthesis using standard methods described in the literature.

The present invention also relates to compounds of formula (I) as defined above, when prepared by a process as described above.

The compounds of formula (I) can be prepared by methods known in the art or as described below in schemes 1 to 4. All starting materials are either commercially available, described in the literature or can be prepared by methods well known in the art. Unless otherwise indicated, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, m and n are as described above

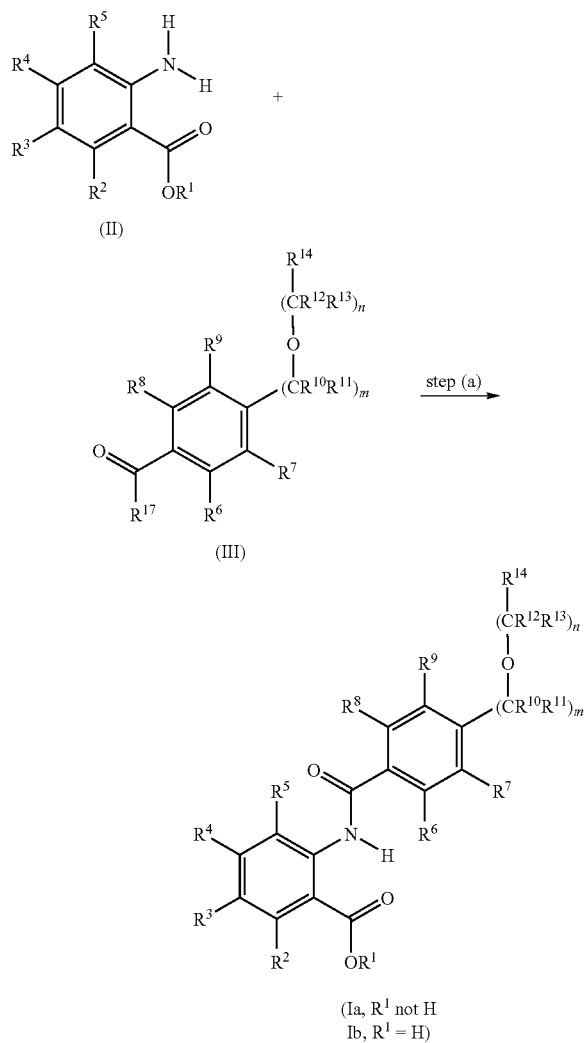

The preparation of compounds of formula (I) is described in scheme 1. Starting anilines II and carboxylic acids III ($R^{17}$=OH), carboxylic acid derivatives III ($R^{17}$=Cl, Br, etc.) or carboxylic acid anhydrides III, particularly symmetric anhydrides, wherein $R^{17}$ is a deprotonated carboxylic acid moiety such as e.g. pivaloylic acid, p-nitrobenzoic acid, p-trifluoromethylbenzoic acid, 2,4,6-trichloro benzoic acid, acetic acid, trifluoroacetic acid, carbonic acid monoisobutyl ester, diphenyl phosphinic acid or benzene sulfonic acid or the remainder of a second moiety of formula (III) bound via an oxygen atom to form a symmetric anhydride, is, are either commercially available, described in the literature or can be prepared by methods well known to a person skilled in the art.

Reacting compounds of formula III with compounds of formula II results in the formation of compounds of formula Ia or Ib (step a). Such amide bond formation reactions are well known in the art. E.g. if $R^{17}$ is equal to chlorine or bromine such an amide bond formation can be performed in a solvent such as dichloromethane, in the presence of a base such as triethylamine, ethyl-diisopropyl-amine or N-ethylmorpholine at temperatures between 0° C. and ambient temperature. Alternatively, compounds of formula Ia or Ib may be prepared by treatment of anilines II with carboxylic acid anhydrides III in a solvent such as dichloromethane, in the presence of a base such as triethylamine, ethyl-diisopropyl-amine or N-ethylmorpholine at temperatures between 0° C. and ambient temperature.

In addition, condensations of amines II with carboxylic acids III ($R^{17}$=OH) can be performed using well known procedures for amide formation, such as the use of N-(3-dimethylaminopropyl)-N'-ethyl-carbodiimide-hydrochloride or BOP (benzotriazol-1-yloxytris(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzo-triazole) in solvents such as dichloromethane, DMF, DMA or dioxane at temperatures between 0° C. and ambient temperature.

If one of the starting materials II or III contains one or more functional groups which are not stable or are reactive under the conditions of the amide bond formation, appropriate protecting groups (as described e.g. in "Protective Groups in Organic Chemistry" by T. W. Greene and P. G. M. Wutts, $2^{nd}$ Ed., 1991, Wiley N.Y.) can be introduced before the condensation step applying methods well known in the art. Such protecting groups can be removed at a later stage of the synthesis using standard methods described in the literature.

Compounds of the general formula Ia and Ib can contain one or more stereocenters and can optionally be separated into optically pure enantiomers or diastereomers by methods well known in the art, e.g. by HPLC chromatography, chromatography on a chiral HPLC column, chromatography with a chiral eluant or by derivatization of compound Ib with an optically pure alcohol to form esters, which can be separated by conventional HPLC chromatography and then converted back to the enantiomerically pure acids Ib ($R^1$=H). In addition, racemic compounds Ib can be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine.

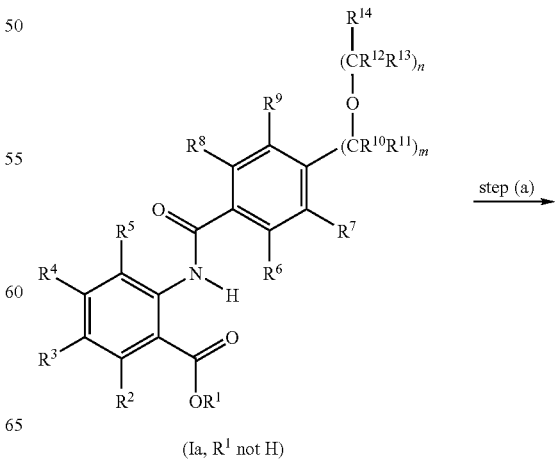

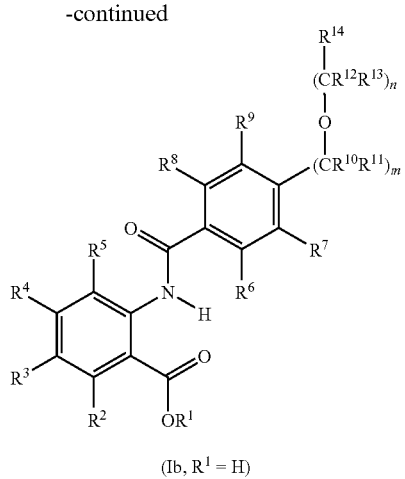

The preparation of compounds of formula Ib with $R^1$=H from compounds of formula Ia with $R^1$ not H is described in scheme 2 (step a). These hydrolysis reactions can be performed according to standard procedures, e.g. by treatment with an alkali hydroxide like LiOH or NaOH in a polar solvent such as tetrahydrofuran, methanol, ethanol or water or mixtures thereof to give carboxylic acids Ib. In case $R^1$ is equal to tert-butyl, treatment with e.g. trifluoroacetic acid, optionally in the presence of anisole in a solvent like dichloromethane or dichloroethane between room temperature and the reflux temperature of the solvents yields carboxylic acids Ib.

If the ester Ia contains one or more functional groups which are not stable under the hydrolysis conditions, appropriate protecting groups (as described e.g. in "Protective Groups in Organic Chemistry" by T. W. Greene and P. G. M. Wutts, $2^{nd}$ Ed., 1991, Wiley N.Y.) can be introduced before the saponification, applying methods well known in the art. Subsequent hydrolysis and removal of the protecting group(s) provides carboxylic acid Ib.

Compounds of the general formula Ib can contain one or more stereocenters and can optionally be separated into optically pure enantiomers or diastereomers by methods well known in the art, e.g. by HPLC chromatography, chromatography on a chiral HPLC column, chromatography with a chiral eluant or by derivatization of compound Ib with an optically pure alcohol to form esters, which can be separated by conventional HPLC chromatography and then converted back to the enantiomerically pure acids Ib. In addition, racemic compounds Ib can be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine.

Scheme 3

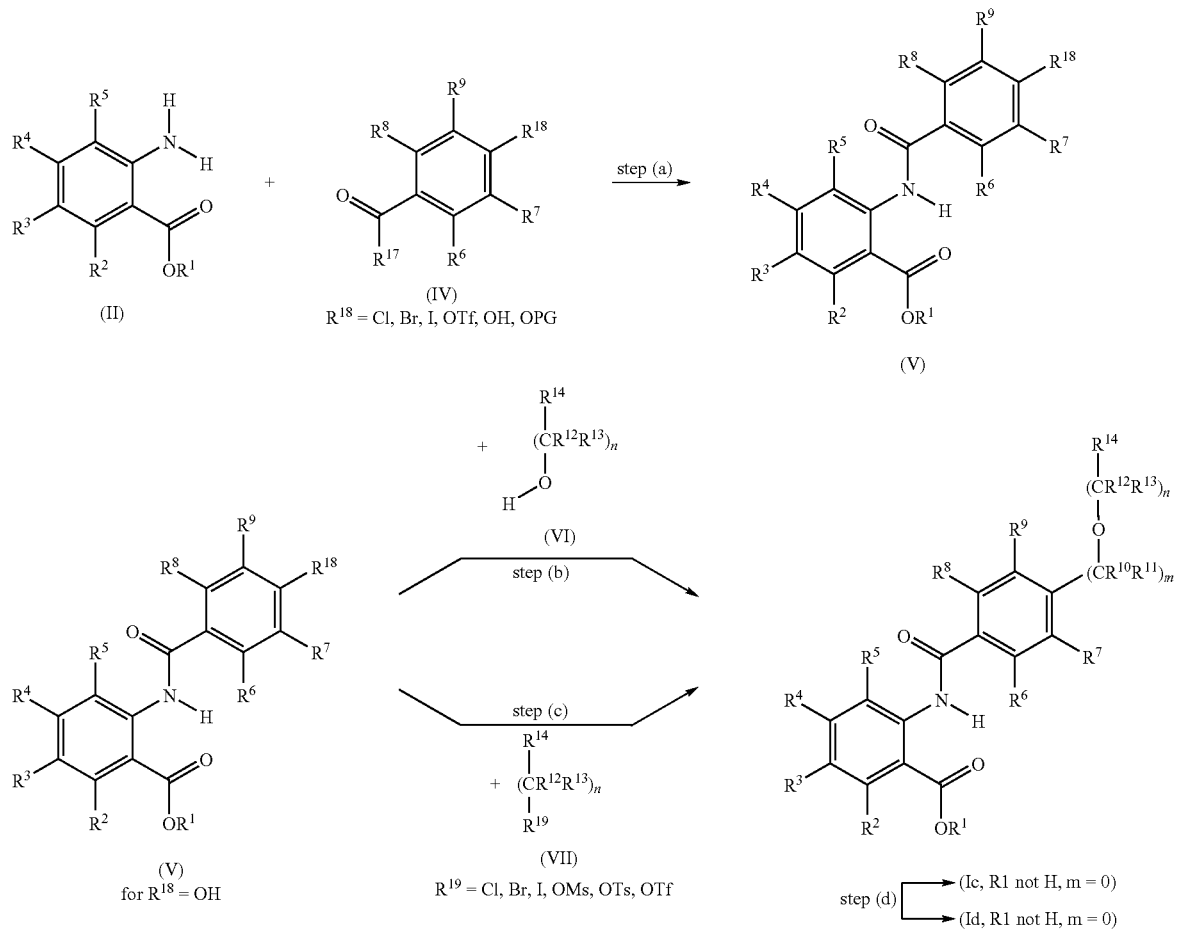

An alternative synthesis for compounds Ic or Id with (($CR^{10}R^{11}$)$_m$, with m=0) is depicted in scheme 3. Carboxylic acids IV ($R^{17}$=OH) and carboxylic acid derivatives IV ($R^{17}$=Cl, Br) or carboxylic acid anhydrides IV are either commercially available, described in the literature or can be prepared by methods well known to a person skilled in the art. Triflates IV ($R^{18}$=OTf) can optionally be prepared from the corresponding phenol derivates IV ($R^{18}$=OH) by standard methods described in the literature, e.g. using PhN(SO$_2$Tf)$_2$ in the presence of a base like cesium carbonate in a solvent like N,N-dimethylformamide at temperatures around ambient temperature or in pyridine with trifluoromethanesulfonic anhydride at 0° C. to ambient temperature. Condensations of anilines II with carboxylic acids IV ($R^{17}$=OH) or carboxylic acid derivatives IV ($R^{17}$=Cl, Br) or carboxylic acid anhydrides IV to give amides V can be performed using standard procedures described in the literature. E.g. if $R^{17}$ is equal to chlorine, bromine or for the carboxylic acid anhydrides the reaction could be performed in a solvent such as dichloromethane, in the presence of a base such as triethylamine, ethyl-diisopropyl-amine or N-ethylmorpholine at temperatures between 0° C. and ambient temperature (step a). If $R^{17}$ is equal to OH activating reagents like e.g. N-(3-dimethylaminopropyl)-N'-ethyl-carbodiimide-hydrochloride or BOP (benzotriazol-1-yloxytris(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzo-triazole) in solvents such as dichloromethane, DMF, DMA or dioxane at temperatures between 0° C. and ambient temperature could be used.

Halides V ($R^{18}$=Cl, Br, I), phenols V ($R^{18}$=OH) or triflates V ($R^{18}$=OTf) can be reacted with alcohols VI to give ethers Ic using methods well known in the art (step b). Phenols V ($R^{18}$=OH) may be generated from the protected phenols V ($R^{18}$=OPG) prior to use by methods well known to the person skilled in the art (as described e.g. in "Protective Groups in Organic Chemistry" by T. W. Greene and P. G. M. Wutts, 2$^{nd}$ Ed., 1991, Wiley N.Y.) and may be converted to the corresponding triflates V ($R^{18}$=OTf) by standard methods described in the literature, e.g. using PhN(SO$_2$Tf)$_2$ in the presence of a base like cesium carbonate in a solvent like N,N-dimethylformamide at temperatures around ambient temperature or in pyridine with trifluoromethanesulfonic anhydride at 0° C. to ambient temperature. The alcohols VI are either commercially available, described in the literature or can be prepared by methods well known to a person skilled in the art. If halides V ($R^{18}$=Cl, Br, I) are used as starting material, compounds Ic can e.g. be prepared in the presence of CuI, cesium carbonate and 8-hydroxychinoline in a solvent like 1-methyl-2-pyrrolidone (see for example Z. J. Song et al., Organic Letters, 4, 1623; 2002). Starting from triflates V ($R^{18}$=OTf), ethers Ic or Id can be synthesized applying e.g. the procedure from Larock et al. (R. C. Larock et al., Organic Letters, 6, 99; 2004) using CsF in acetonitrile at ambient temperature. In addition, several transition metal mediated procedures for the formation of aryl ethers are reported in the literature (see e.g. J. F. Hartwig et al., J. Am. Chem. Soc., 121, 3224; 1999).

Alternatively, phenols V ($R^{18}$=OH) may be treated with alcohols VI using *Mitsunobu* (e.g. O. Mitsunobu, *Synthesis* 1981, 1.) conditions to yield compounds Ic. This transformation is preferably carried out with triphenylphosphine and di-tert-butyl-, diisopropyl- or diethyl-azodicarboxylate as reagents, in a solvent like toluene, dichloromethane or tetrahydrofuran at 0° C. to ambient temperature.

Alternatively, compounds Ic and Id may be prepared from phenol V ($R^{18}$=OH) by alkylation with compounds VII ($R^{19}$=Br, Cl, I, MsO, TsO, TfO) in solvents such as acetone, acetonitrile, DMF, DMA or THF in the presence of bases such as K$_2$CO$_3$, Cs$_2$CO$_3$ or ethyl-diisopropyl-amine at ambient temperature to reflux (step c).

Aryl ethers Ic with an ester group ($R^1 \neq H$) can be hydrolyzed according to standard procedures, e.g. by treatment with an alkali hydroxide like LiOH or NaOH in a polar solvent mixture like tetrahydrofurane/ethanol/water to give carboxylic acids of formula Id ($R^1$=H) (step d). In case $R^1$ is equal to tert-butyl, treatment with e.g. trifluoroacetic acid, optionally in the presence of anisole in a solvent like dichloromethane or dichloroethane between room temperature and the reflux temperature of the solvents yields carboxylic acids Id (step d).

If one of the starting materials II, IV, V, VI, or VII contains one or more functional groups which are not stable or are reactive under the conditions of the amide bond formation, appropriate protecting groups (as described e.g. in "Protective Groups in Organic Chemistry" by T. W. Greene and P. G. M. Wutts, 2$^{nd}$ Ed., 1991, Wiley N.Y.) can be introduced before the condensation step, applying methods well known in the art. Such protecting groups can be removed at a later stage of the synthesis using standard methods described in the literature.

Compounds of the general formula Ic and Id can contain one or more stereocenters and can optionally be separated into optically pure enantiomers or diastereomers by methods well known in the art, e.g. by HPLC chromatography, chromatography on a chiral HPLC column, chromatography with a chiral eluant or by derivatization of compounds Id with an optically pure alcohol to form esters, which can be separated by conventional HPLC chromatography and then converted back to the enantiomerically pure acids Id. In addition, racemic compounds Id can be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine.

Scheme 4

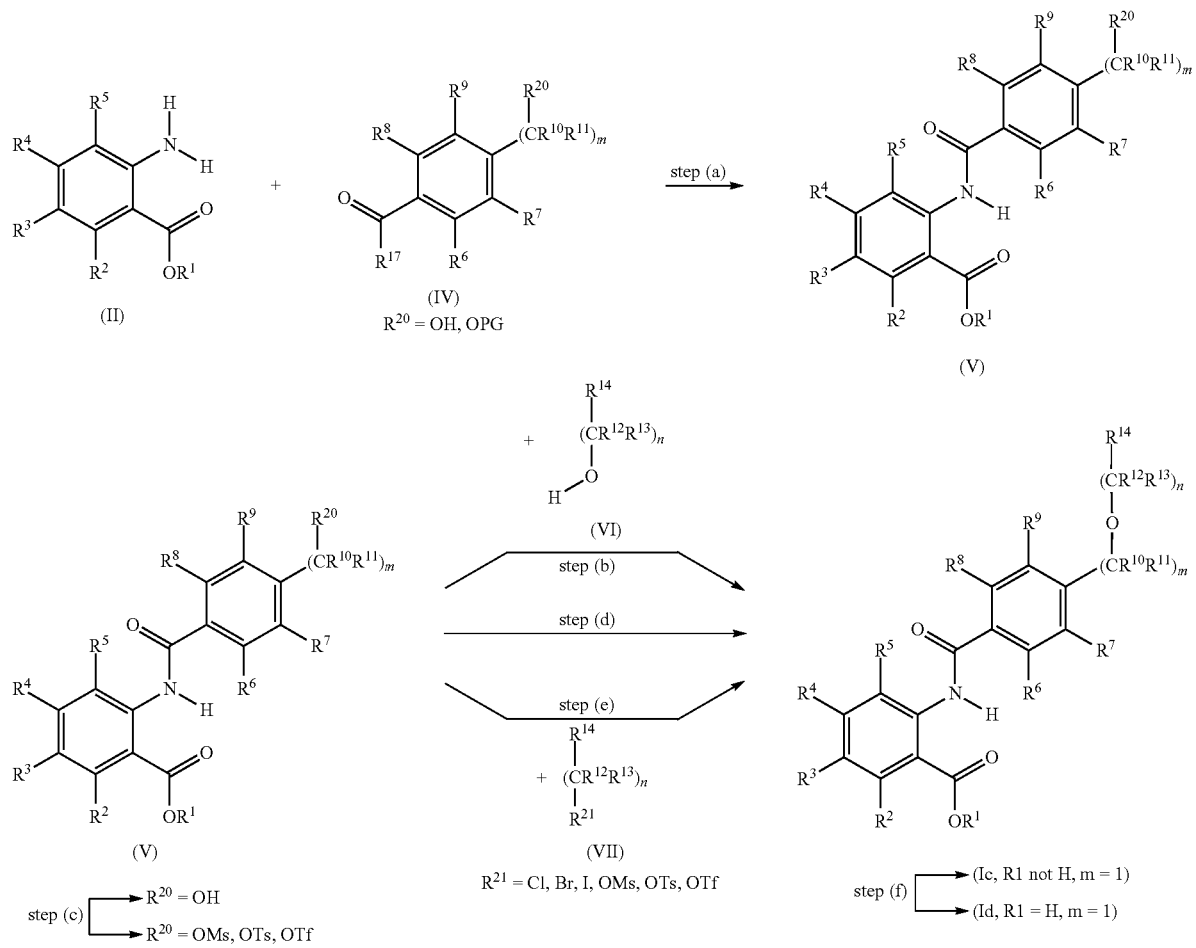

An alternative synthesis for compounds Ic or Id (m=1) is depicted in scheme 4. Carboxylic acids IV ($R^{20}$=OH, OPG) and carboxylic acid derivatives IV ($R^{17}$=Cl, Br) or carboxylic acid anhydrides IV are either commercially available, described in the literature or can be prepared by methods well known to a person skilled in the art. Condensations of anilines II with carboxylic acids IV ($R^{17}$=OH) or carboxylic acid derivatives IV ($R^7$=Cl, Br) or carboxylic acid anhydrides IV to give amides V can be performed using standard procedures described in the literature. E.g. if $R^{17}$ is equal to chlorine or bromine or for the carboxylic acid anhydrides the reaction could be performed in a solvent such as dichloromethane, in the presence of a base such as triethylamine, ethyl-diisopropyl-amine or N-ethylmorpholine at temperatures between 0° C. and ambient temperature (step a). If $R^{17}$ is equal to OH activating reagents like e.g. N-(3-dimethylaminopropyl)-N'-ethyl-carbodiimide-hydrochloride or BOP (benzotriazol-1-yloxytris(dimethylamino)phosphonium hexafluorophosphate) in the presence of a base such as ethyl-diisopropyl-amine, triethylamine, N-methylmorpholine optionally in the presence of 4-dimethylamino-pyridine or HOBt (1-hydroxy-benzo-triazole) in solvents such as dichloromethane, DMF, DMA or dioxane at temperatures between 0° C. and ambient temperature could be used.

Alcohols V ($R^{20}$=OH) can be reacted with alcohols VI to give ethers Ic using methods well known in the art (step b). Alcohols V may be generated from the protected alcohols V ($R^{20}$OPG) prior to use by methods well known to the person skilled in the art (as described e.g. in "Protective Groups in Organic Chemistry" by T. W. Greene and P. G. M. Wutts, $2^{nd}$ Ed., 1991, Wiley N.Y.). The alcohols VI are either commercially available, described in the literature or can be prepared by methods well known to a person skilled in the art. For the reaction of alcohols V with alcohols VI (n=0) Mitsunobu conditions may be used to give compounds Ic. This transformation is preferably carried out with triphenylphosphine and di-tert-butyl-, diisopropyl- or diethyl-azodicarboxylate as reagents, in a solvent like toluene, dichloromethane or tetrahydrofuran at 0° C. to ambient temperature.

Alternatively, alcohol V may be converted to the corresponding mesylate or tosylate V ($R^{20}$=OMs, OTs) by treatment with methanesulfonyl chloride or para-toluenesulfonyl chloride, respectively, in $CH_2Cl_2$ in the presence of a base such as pyridine or ethyl-diisopropyl-amine optionally in the presence of DMAP at temperatures between 0° C. to ambient temperature (step c). The corresponding triflates V ($R^{20}$=OTf) may be prepared in pyridine with trifluoromethanesulfonic anhydride at 0° C. to ambient temperature. Reaction of compounds V ($R^{20}$=OMs, OTs, OTf) with alcohols VI in the presence of sodium hydride in solvents such as DMF or THF at temperatures between 0° C. to reflux of the solvent gives compounds Ic (step d).

Alternatively, compounds Ic and Id may be prepared from alcohol V ($R^{20}$=OH) by alkylation with compounds VII ($R^{21}$=Br, Cl, I, MsO, TsO, TfO) in the presence of sodium hydride in solvents such as DMF or THF at temperatures between 0° C. to reflux of the solvent (step e).

Aryl ethers Ic with an ester group ($R^1$≠H) can be hydrolyzed according to standard procedures, e.g. by treatment with an alkali hydroxide like LiOH or NaOH in a polar solvent mixture like tetrahydrofurane/ethanol/water to give carboxylic acids of formula Id ($R^1$=H) (step f). In case $R^1$ is equal to tert-butyl, treatment with e.g. trifluoroacetic acid, optionally in the presence of anisole in a solvent like dichloromethane or dichloroethane between room temperature and the reflux temperature of the solvents yields carboxylic acids Id (step d).

If one of the starting materials II, IV, V, VI, or VII contains one or more functional groups which are not stable or are reactive under the conditions of the amide bond formation, appropriate protecting groups (as described e.g. in "Protective Groups in Organic Chemistry" by T. W. Greene and P. G. M. Wutts, $2^{nd}$ Ed., 1991, Wiley N.Y.) can be introduced before the condensation step applying methods well known in the art. Such protecting groups can be removed at a later stage of the synthesis using standard methods described in the literature.

Compounds of the general formula Ic and Id can contain one or more stereocenters and can optionally be separated into optically pure enantiomers or diastereomers by methods well known in the art, e.g. by HPLC chromatography, chromatography on a chiral HPLC column, chromatography with a chiral eluant or by derivatization of acids Id with an optically pure alcohol to form esters, which can be separated by conventional HPLC chromatography and then converted back to the enantiomerically pure acids Id. In addition, racemic compounds Id can be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine.

Compounds of the general formula Ic/Id can contain one or more stereocenters and can optionally be separated into optically pure enantiomers or diastereomers by methods well known in the art, e.g. by HPLC chromatography, chromatography on a chiral HPLC column, chromatography with a chiral eluant or by derivatization with an optically pure alcohol to form esters, which can be separated by conventional HPLC chromatography and then converted back to the enantiomerically pure acids Id. In addition, racemic compounds can be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine.

The conversion of a compound of formula (I) into a pharmaceutically acceptable salt can be carried out by treatment of such a compound with physiologically compatible bases. Examples of such salts are alkaline, earth-alkaline and ammonium salts such as e.g. Na-, K-, Ca- and trimethylammonium-salt. One method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofurane-water mixture) and to remove the solvent by evaporation or lyophilisation The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU). Pharmaceutically acceptable esters can furthermore be prepared by treatment of a suitable hydroxy group present in the molecule with a suitable acid, optionally or if necessary in the presence of a condensating agent as described above.

Insofar as their preparation is not described in the examples, the compounds of formula (I) as well as all intermediate products can be prepared according to analogous methods or according to the methods set forth above. Starting materials are commercially available or known in the art.

As described above, the compounds of formula (I) of the present invention and compounds selected from the group consisting of:
- 5-chloro-2-[[2,3-dimethyl-4-[1-[4-(2-methylpropyl)phenyl]ethoxy]benzoyl]amino]-benzoic acid,
- 2-[[4-[(4-bromophenoxy)methyl]benzoyl]amino]-benzoic acid methyl ester,
- 2-[(4-phenoxybenzoyl)amino]-benzoic acid,
- 2-[[4-[(3-methoxyphenoxy)methyl]benzoyl]amino]-benzoic acid methyl ester,
- 2-[[4-[(4-methoxyphenoxy)methyl]benzoyl]amino]-benzoic acid,
- 2-[[4-[(2-methoxyphenoxy)methyl]benzoyl]amino]-benzoic acid methyl ester,
- 2-[[4-[(2,4-dichlorophenoxy)methyl]benzoyl]amino]-benzoic acid methyl ester,
- 2-[[4-[[4-(1,1-dimethylethyl)phenoxy]methyl]benzoyl]amino]-benzoic acid methyl ester,
- 2-[[4-[(2-chloro-6-fluorophenyl)methoxy]benzoyl]amino]-benzoic acid methyl ester,
- 2-[[4-[(2-chlorophenoxy)methyl]benzoyl]amino]-benzoic acid methyl ester,
- 2-[[4-[(2-chlorophenyl)methoxy]benzoyl]amino]-benzoic acid methyl ester,
- 2-[[4-[(4-propylphenoxy)methyl]benzoyl]amino]-benzoic acid methyl ester, and
- 2-[[4-[(2-chlorophenoxy)methyl]benzoyl]amino]-benzoic acid 1-methylethyl ester, can be used as medicaments for the treatment and/or prevention of diseases which are modulated by HM74A agonists. Examples of such diseases are increased lipid and cholesterol levels, particularly dyslipidemia, low HDL-cholesterol, atherosclerotic diseases, hypertriglyceridemia, thrombosis, angina pectoris, peripheral vascular disease, stroke, diabetes, particularly non-insulin dependent diabetes mellitus, metabolic syndrome, Alzheimer's disease, Parkinson's disease, schizophrenia, sepsis, inflammatory diseases (such as e.g. colitis, pancreatitis, cholestasis/fibrosis of the liver, and diseases that have an inflammatory component such as e.g. Alzheimer's disease or impaired/improvable cognitive function). The use as medicament for the treatment of atherosclerosis, low HDL cholesterol levels, non-insulin dependent diabetes mellitus, and the metabolic syndrome is preferred.

The invention therefore also relates to pharmaceutical compositions comprising a compound as described above or a compound selected from the group consisting of:
- 5-chloro-2-[[2,3-dimethyl-4-[1-[4-(2-methylpropyl)phenyl]ethoxy]benzoyl]amino]-benzoic acid,
- 2-[[4-[(4-bromophenoxy)methyl]benzoyl]amino]-benzoic acid methyl ester,
- 2-[(4-phenoxybenzoyl)amino]-benzoic acid, 2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester,
and a pharmaceutically acceptable carrier and/or adjuvant.

Further, the invention relates to compounds as described above or compounds selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester,
for use as therapeutic active substances, especially as therapeutic active substances for the treatment and/or prevention of diseases which are modulated by HM74A agonists, particularly as therapeutically active substances for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, colitis, pancreatitis and cholestasisfibrosis of the liver.

In another embodiment, the invention relates to a method for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, colitis, pancreatitis and cholestasisfibrosis of the liver, which method comprises administering a compound as described above or a compound selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester, to a human or animal.

The invention further relates to the use of compounds as defined above or compounds selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester,
for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, colitis, pancreatitis and cholestasisfibrosis of the liver.

In addition, the invention relates to the use of compounds as described above or compounds selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester,
for the preparation of medicaments for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, colitis, pancreatitis and cholestasisfibrosis of the liver. Such medicaments comprise a compound as described above.

Prevention and/or treatment of atherosclerosis, low HDL cholesterol levels, non-insulin dependent diabetes mellitus, and the metabolic syndrome is preferred.

In the above mentioned compositions, uses and methods, compounds of formula (I) as described above are preferred over the compounds selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester.

In the compositions, methods and uses described above, of the compounds selected from the group consisting of:
5-chloro-2-[[2,3-dimethyl-4-[1-[4-(2-methylpropyl)phenyl]ethoxy]benzoyl]amino]-benzoic acid,
2-[[4-[(4-bromophenoxy)methyl]benzoyl]amino]-benzoic acid methyl ester,
2-[(4-phenoxybenzoyl)amino]-benzoic acid,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester, the compounds selected from the group consisting of:
2-[[4-[(4-bromophenoxy)methyl]benzoyl]amino]-benzoic acid methyl ester,
2-[[4-[(3-methoxyphenoxy)methyl]benzoyl]amino]-benzoic acid methyl ester,
2-[[4-[(4-methoxyphenoxy)methyl]benzoyl]amino]-benzoic acid,
2-[[4-[(2-methoxyphenoxy)methyl]benzoyl]amino]-benzoic acid methyl ester,
2-[[4-[(2,4-dichlorophenoxy)methyl]benzoyl]amino]-benzoic acid methyl ester,
2-[[4-[[4-(1,1-dimethylethyl)phenoxy]methyl]benzoyl]amino]-benzoic acid methyl ester,
2-[[4-[(2-chloro-6-fluorophenyl)methoxy]benzoyl]amino]-benzoic acid methyl ester,
2-[[4-[(2-chlorophenoxy)methyl]benzoyl]amino]-benzoic acid methyl ester,
2-[[4-[(2-chlorophenyl)methoxy]benzoyl]amino]-benzoic acid methyl ester,
2-[[4-[(4-propylphenoxy)methyl]benzoyl]amino]-benzoic acid methyl ester, and
2-[[4-[(2-chlorophenoxy)methyl]benzoyl]amino]-benzoic acid 1-methylethyl ester,
are preferred.

The following tests were carried out in order to determine the biological activity of the compounds of formula (I).

Primary Radiolabelled Ligand Competition Binding Assay

Nicotinic acid binding assays were performed with membrane preparations. A cell pellet containing $1\times10^8$ HEK-293 cells, stably transfected with the HM74A receptor, was resuspended in 3 ml of ice cold Dounce Buffer (10 mM Tris-Cl p.H 7.6, 0.5 mM $MgCl_2$) supplemented with Roche protease inhibitor cocktail and homogenized at high speed on a Polytron homogenizer two times for 20 sec on ice. Nuclei and unbroken cells were removed by centrifugation for 5 min at 1,000×g after the addition of 1 ml of tonicity restoration buffer (10 mM Tris pH 7.6, 0.5 mM $MgCl_2$, 600 mM NaCl). The homogenate was centrifuged at 60,000×g for 30 min and pellets were resuspended in Tris buffer (50 mM Tris pH 7.4, containing protease inhibitors). Binding reactions contained 20 µg membranes as determined by BCA protein assay (Pierce), 50 nM [$^3$H]-nicotinic acid (Amersham) with or without compound addition in 250 µl of binding buffer (50 mM Tris pH 7.4, 2 mM $MgCl_2$, 0.02% CHAPS). Incubations were carried out at room temperature for 2 hrs and terminated by filtration using a Filtermate Harvester (PerkinElmer) onto GF/C filter plates (Millipore). Bound [$^3$H]-nicotinic acid was determined by scintillation counting using Top Count NXT (PerkinElmer). Compounds were dissolved in a concentration of $10^{-2}$ or $10^{-3}$ M in DMSO, further dilutions were performed in binding buffer. The effects of compounds were expressed as % inhibition of [$^3$H]-nicotinic acid binding. Sigmoidal curves were fitted using the XLfit3 program (ID Business Solutions Ltd. UK) and $IC_{50}$ values determined.

The compounds of the present invention exhibit IC 50 values in a range of about 0.001 µM to about 100 µM in the binding assay. Preferably, the compounds of the present invention have $IC_{50}$ values in a range of about 0.001 µM to about 10.0 µM, more preferably about 0.001 µM to about 1 µM.

Secondary Fluorescent Calcium Indicator Assay (FLIPR)

HEK-293 cells were grown in tissue culture medium (DMEM/Nut mix F12 Medium with Glutamax I (Invitrogen), containing 10% FBS) at 37° C. in a 5% $CO_2$ atmosphere. These cells were cultured in 6-well dishes at $3\times10^5$ cells/well and double transfected with DNA vectors (pcDNA3.1, Invitrogen) expressing either HM74A or HM74 and the chimeric G protein Gqi9. Two days after transfection the wells were combined and plated in 150 $cm^2$ flasks, in the presence of 50 µg/ml Hygromycin (Invitrogen) and 500 µg/ml Geneticin (Gibco). Fourteen days after plating, colonies were picked, expanded and analyzed for expression using a functional assay (FLIPR). Stable transfected HEK-293 cells expressing either HM74A or HM74 and the chimeric G protein Gqi9 were plated at 50,000 cells/well in black 96-well plates with clear bottom (Costar) and cultured to confluency overnight in growth media (DMEM/Nut mix F12 Medium with Glutamax I (Invitrogen), containing 10% FBS) at 37° C. in a humidified cell incubator containing 5% $CO_2$. Growth media was aspirated and replaced with 100 µl of 1×FLIPR Calcium Assay Dye (Molecular Devices) in Hank's balanced salt solution (HBSS) containing 10 mM HEPES, and 250 mM probenecid (Sigma), for 1 hour at 37° C. Cell plates were transferred to a FLIPR unit (Molecular Devices), and 50 µl of 3× compound dilution were added. Fluorescence emissions were measured and the effects of compounds were expressed as % stimulation of maximal nicotinic acid response (100 µM). Sigmoidal curves were fitted using the XLfit3 program (ID Business Solutions Ltd. UK) and $EC_{50}$ values determined.

The compounds of the present invention exhibit $EC_{50}$ values in a range of about 0.001 µM about 100 µM in the FLIPR assay. Preferably, the compounds of the present invention have $EC_{50}$ values in a range of about 0.001 µM to about 10.0 µM; more preferably about 0.001 µM to about 1 µM.

In the following table, EC50 values for some of the compounds of the present invention are shown.

| Example | $EC_{50}$ HM74A [µM] |
|---|---|
| 2 | 1.100 |
| 17 | 0.529 |
| 29 | 0.101 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 5000 mg, preferably about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-1000 mg, preferably 1-300 mg, more preferably 1-100 mg, of a compound of formula I.

The following Examples serve to illustrate the present invention in more detail. They are, however, not intended to limit its scope in any manner.

EXAMPLES

General Remarks

The reactions were performed under argon where appropriate.

Example 1

2-(4-Benzyloxy-benzoylamino)-benzoic acid

Step 1

2-(4-Benzyloxy-benzoylamino)-benzoic acid methyl ester

To 2-amino-benzoic acid methyl ester (0.51 mL) and triethylamine (0.69 mL) in dichloromethane (31 mL) at −50° C. was slowly added a solution of 4-benzyloxy-benzoyl chloride [1486-50-6] (1 g) in 31 mL of dichloromethane. The reaction mixture was then allowed to warm up to room temperature and stirred for an additional hour. After such time, the reaction mixture was washed with water. The aqueous phase was further extracted with dichloromethane. The combined organic phases were dried over sodium sulfate and concentrated in vacuo. The residue was purified by column chromatography (heptane-ethyl acetate: 0-50%) to yield 2-(4-benzyloxy-benzoylamino)-benzoic acid methyl ester (400 mg). MS (m/e): 362.5 (M+H$^+$, 100%).

Step 2

2-(4-Benzyloxy-benzoylamino)-benzoic acid

To 2-(4-benzyloxy-benzoylamino)-benzoic acid methyl ester (50 mg) in methanol (3 mL) was added lithium hydroxide monohydrate (6.3 mg) and the reaction mixture was stirred at room temperature until the reaction was complete. The reaction mixture was then reacidified using 1N HCl and the product was then purified by column chromatography (SiO$_2$, ethyl acetate-ethanol: 0-20%) to give 2-(4-benzyloxy-benzoylamino)-benzoic acid as a white solid (39 mg). MS (m/e): 346.3 (M−H$^-$, 100%).

Example 2

2-[4-(4-Fluoro-phenoxy)-benzoylamino]-benzoic acid

To 2-(4-iodo-benzoylamino)-benzoic acid methyl ester [75541-84-3] (50 mg) in 1-methyl-2-pyrrolidinone (1 mL) was added 4-fluorophenol (29.4 mg), copper (I) chloride (6.6 mg), cesium carbonate (85 mg) and 8-hydroxy-chinolin (4.7 mg). The reaction mixture was stirred at 120° C. for 18 hours. After such time, the reaction mixture was allowed to cool down to room temperature, diluted with water, formic acid was added (0.3 mL) and the solution was purified by preparative HPLC to yield 2-[4-(4-fluoro-phenoxy)-benzoylamino]-benzoic acid (49.1 mg). MS (m/e): 332.1 (M−H$^-$, 100%).

Example 3

2-[4-(3,4-Dichloro-phenoxy)-benzoylamino]-benzoic acid

In analogy to example 2, 2-[4-(3,4-Dichloro-phenoxy)-benzoylamino]-benzoic acid was prepared from 2-(4-iodo-benzoylamino)-benzoic acid methyl ester [75541-84-3] and 3,4-dichlorophenol. MS (m/e): 400.0 (M−H$^-$, 100%).

Example 4

2-(4-p-Tolyloxy-benzoylamino)-benzoic acid

In analogy to example 2, 2-(4-p-Tolyloxy-benzoylamino)-benzoic acid was prepared from 2-(4-iodo-benzoylamino)-benzoic acid methyl ester [75541-84-3] and p-cresol. MS (m/e): 346.3 (M−H$^-$, 100%).

Example 5

2-[4-(3-Methoxy-phenoxy)-benzoylamino]-benzoic acid

In analogy to example 2, 2-[4-(3-Methoxy-phenoxy)-benzoylamino]-benzoic acid was prepared from 2-(4-iodo-benzoylamino)-benzoic acid methyl ester [75541-84-3] and 3-methoxy-phenol. MS (m/e): 362.4 (M−H$^-$, 100%).

Example 6

2-(4-o-Tolyloxy-benzoylamino)-benzoic acid

In analogy to example 2, 2-(4-o-Tolyloxy-benzoylamino)-benzoic acid was prepared from 2-(4-iodo-benzoylamino)-benzoic acid methyl ester [75541-84-3] and o-cresol. MS (m/e): 346.1 (M−H$^-$, 100%).

Example 7

2-[4-(4-Methoxy-phenoxy)-benzoylamino]-benzoic acid

In analogy to example 2, 2-[4-(4-Methoxy-phenoxy)-benzoylamino]-benzoic acid was prepared from 2-(4-iodo-benzoylamino)-benzoic acid methyl ester [75541-84-3] and 4-methoxy-phenol. MS (m/e): 362.4 (M−H$^-$, 100%).

Example 8

2-[4-(4-Chloro-phenoxy)-benzoylamino]-benzoic acid

In analogy to example 2, 2-[4-(4-Chloro-phenoxy)-benzoylamino]-benzoic acid was prepared from 2-(4-iodo-benzoylamino)-benzoic acid methyl ester [75541-84-3] and 4-chloro-phenol. MS (m/e): 366.1 (M−H$^-$, 100%).

Example 9

2-[4-(3,4-Difluoro-phenoxy)-benzoylamino]-benzoic acid

In analogy to example 2, 2-[4-(3,4-Difluoro-phenoxy)-benzoylamino]-benzoic acid was prepared from 2-(4-iodobenzoylamino)-benzoic acid methyl ester [75541-84-3] and 3,4-difluoro-phenol. MS (m/e): 368.3 (M–H⁻, 100%).

Example 10

2-[4-(4-Methanesulfonyl-phenoxy)-benzoylamino]-benzoic acid

In analogy to example 2, 2-[4-(4-Methanesulfonyl-phenoxy)-benzoylamino]-benzoic acid was prepared from 2-(4-iodo-benzoylamino)-benzoic acid methyl ester [75541-84-3] and 4-(methylsulfonyl)-phenol. MS (m/e): 368.3 (M–H⁻, 100%).

Example 11

2-{4-[4-Methoxycarbonyl)phenoxy]benzoyl}aminobenzoic acid

In analogy to example 2, 2-{4-[4-Methoxycarbonyl)phenoxy]benzoyl}aminobenzoic acid was prepared from 2-(4-iodo-benzoylamino)-benzoic acid methyl ester [75541-84-3] and 4-hydroxy-benzoic acid methyl ester. MS (m/e): 390.3 (M–H⁻, 100%).

Example 12

2-[4-(3,5-Dichloro-phenoxy)-benzoylamino]-benzoic acid

In analogy to example 2, 2-[4-(3,5-Dichloro-phenoxy)-benzoylamino]-benzoic acid was prepared from 2-(4-iodo-benzoylamino)-benzoic acid methyl ester [75541-84-3] and from 3,5-dichloro-phenol. MS (m/e): 400.1 (M–H⁻, 100%).

Example 13

2-[4-(4-Cyano-phenoxy)-benzoylamino]-benzoic acid

In analogy to example 2, 2-[4-(4-Cyano-phenoxy)-benzoylamino]-benzoic acid was prepared from 2-(4-iodo-benzoylamino)-benzoic acid methyl ester [75541-84-3] and 4-hydroxybenzonitrile. MS (m/e): 357.1 (M–H⁻, 100%).

Example 14

2-[4-(2-Fluoro-phenoxy)-benzoylamino]-benzoic acid

In analogy to example 2, 2-[4-(2-Fluoro-phenoxy)-benzoylamino]-benzoic acid was prepared from 2-(4-iodo-benzoylamino)-benzoic acid methyl ester [75541-84-3] and 2-fluorophenol. MS (m/e): 350.4 (M–H⁻, 100%).

Example 15

2-[4-(2-Chloro-phenoxy)-benzoylamino]-benzoic acid

In analogy to example 2, 2-[4-(2-Chloro-phenoxy)-benzoylamino]-benzoic acid was prepared from 2-(4-iodo-benzoylamino)-benzoic acid methyl ester [75541-84-3] and 2-chloro-phenol. MS (m/e): 365.9 (M–H⁻, 100%).

Example 16

2-[4-(3-Fluoro-phenoxy)-benzoylamino]-benzoic acid

In analogy to example 2, 2-[4-(3-Fluoro-phenoxy)-benzoylamino]-benzoic acid was prepared from 2-(4-iodo-benzoylamino)-benzoic acid methyl ester [75541-84-3] and 3-fluoro-phenol. MS (m/e): 350.0 (M–H⁻, 100%).

Example 17

2-[4-(3-Chloro-phenoxy)-benzoylamino]-benzoic acid

In analogy to example 2, 2-[4-(3-Chloro-phenoxy)-benzoylamino]-benzoic acid was prepared from 2-(4-iodo-benzoylamino)-benzoic acid methyl ester [75541-84-3] and 3-chloro-phenol. MS (m/e): 366.0 (M–H⁻, 100%).

Example 18

2-(4-m-Tolyloxy-benzoylamino)-benzoic acid

In analogy to example 2, 2-(4-m-Tolyloxy-benzoylamino)-benzoic acid was prepared from 2-(4-iodo-benzoylamino)-benzoic acid methyl ester [75541-84-3] and m-cresol. MS (m/e): 346.3 (M–H⁻, 100%).

Example 19

2-[4-(Quinolin-8-yloxy)-benzoylamino]-benzoic acid

In analogy to example 2, 2-[4-(Quinolin-8-yloxy)-benzoylamino]-benzoic acid was prepared from 2-(4-iodo-benzoylamino)-benzoic acid methyl ester [75541-84-3] and quinolin-8-ol. MS (m/e): 383.0 (M–H⁻, 100%).

Example 20

2-[4-(4-Trifluoromethyl-phenoxy)-benzoylamino]-benzoic acid

In analogy to example 2, 2-[4-(4-Trifluoromethyl-phenoxy)-benzoylamino]-benzoic acid was prepared from 2-(4-iodo-benzoylamino)-benzoic acid methyl ester [75541-84-3] and 4-trifluororomethyl phenol. MS (m/e): 399.8 (M–H⁻, 100%).

Example 21

2-[4-(4-Carbamoyl-phenoxy)-benzoylamino]-benzoic acid

In analogy to example 2, 2-[4-(4-Carbamoyl-phenoxy)-benzoylamino]-benzoic acid was prepared from 2-(4-iodo-benzoylamino)-benzoic acid methyl ester [75541-84-3] and 4-hydroxy-benzamide. MS (m/e): 375.0 (M–H⁻, 100%).

Example 22

2-[4-(4-Dimethylaminomethyl-phenoxy)-benzoylamino]-benzoic acid

In analogy to example 2, 2-[4-(4-Dimethylaminomethyl-phenoxy)-benzoylamino]-benzoic acid was prepared from 2-(4-iodo-benzoylamino)-benzoic acid methyl ester [75541-84-3] and 4-dimethylaminomethyl-phenol. MS (m/e): 389.0 (M−H⁻, 100%).

Example 23

2-[4-(4-[1,2,4]Triazol-1-yl-phenoxy)-benzoylamino]-benzoic acid

In analogy to example 2, 2-[4-(4-[1,2,4]Triazol-1-yl-phenoxy)-benzoylamino]-benzoic acid was prepared from 2-(4-iodo-benzoylamino)-benzoic acid methyl ester [75541-84-3] and 4-[1,2,4]triazol-1-yl-phenol. MS (m/e): 398.9 (M−H⁻, 100%).

Example 24

2-[4-(2,4-Difluoro-phenoxy)-benzoylamino]-benzoic acid

In analogy to example 2,-[4-(2,4-Difluoro-phenoxy)-benzoylamino]-benzoic acid was prepared from 2-(4-iodo-benzoylamino)-benzoic acid methyl ester [75541-84-3] and 2,4-difluoro-phenol. MS (m/e): 367.1 (M−H⁻, 100%).

Example 25

2-[4-(Pyridin-2-yloxy)-benzoylamino]-benzoic acid

In analogy to example 2, 2-[4-(Pyridin-2-yloxy)-benzoylamino]-benzoic acid was prepared from 2-(4-iodo-benzoylamino)-benzoic acid methyl ester [75541-84-3] and 2-hydroxypyridine. MS (m/e): 333.4 (M−H⁻, 100%).

Example 26

2-[4-(Pyridin-3-yloxy)-benzoylamino]-benzoic acid

In analogy to example 2, 2-[4-(Pyridin-3-yloxy)-benzoylamino]-benzoic acid was prepared from 2-(4-iodo-benzoylamino)-benzoic acid methyl ester [75541-84-3] and 3-hydroxypyridine. MS (m/e): 333.3 (M−H⁻, 100%).

Example 27

2-[4-(3,4-Dimethyl-phenoxy)-benzoylamino]-benzoic acid

In analogy to example 2, 2-[4-(3,4-Dimethyl-phenoxy)-benzoylamino]-benzoic acid was prepared from 2-(4-iodo-benzoylamino)-benzoic acid methyl ester [75541-84-3] and 3,4-dimethylphenol. MS (m/e): 362.4 (M−H⁻, 100%).

Example 28

2-[4-(2,3-Difluoro-phenoxy)-benzoylamino]-benzoic acid

In analogy to example 2, 2-[4-(2,3-Difluoro-phenoxy)-benzoylamino]-benzoic acid was prepared from 2-(4-iodo-benzoylamino)-benzoic acid methyl ester [75541-84-3] and 2,3-difluorophenol. MS (m/e): 368.1 (M−H⁻, 100%).

Example 29

2-[4-(2,5-Difluoro-phenoxy)-benzoylamino]-benzoic acid

In analogy to example 2, 2-[4-(2,5-Difluoro-phenoxy)-benzoylamino]-benzoic acid was prepared from 2-(4-iodo-benzoylamino)-benzoic acid methyl ester [75541-84-3] and 2,5-difluorophenol. MS (m/e): 368.1 (M−H⁻, 100%).

Example 30

2-(3-Methyl-4-phenoxy-benzoylamino)-benzoic acid

Step 1

2-(4-Bromo-3-methyl-benzoylamino)-benzoic acid methyl ester

To 2-amino-benzoic acid methyl ester (3.1 g) in dichloromethane (31 mL) was slowly added 4-bromo-3-methyl-benzoyl chloride [21900-25-4] (4.8 g) and triethylamine (3.1 mL). The reaction mixture was then stirred at room temperature for 1 hour. After such time, the reaction mixture was further diluted with dichloromethane (50 mL) and washed with water. The combined aqueous phase was further extracted with dichloromethane. All combined organic phases were then dried over sodium sulfate and concentrated in vacuo. The residue was then recrystallised from ethanol to give 2-(4-bromo-3-methyl-benzoylamino)-benzoic acid methyl ester (6.14 g) as white crystals, m.p.=123° C. MS (m/e): 348.3 (M+H⁺, 100%).

Step 2

2-(3-Methyl-4-phenoxy-benzoylamino)-benzoic acid

In analogy to example 2,2-(3-Methyl-4-phenoxy-benzoylamino)-benzoic acid was prepared from 2-(4-bromo-3-methyl-benzoylamino)-benzoic acid methyl ester and phenol. MS (m/e): 346.3 (M−H⁻, 100%).

Example 31

2-(2-Methyl-4-phenoxy-benzoylamino)-benzoic acid

In analogy to example 30, 2-(2-Methyl-4-phenoxy-benzoylamino)-benzoic acid was prepared using 4-bromo-2-methyl-benzoyl chloride [21900-45-8] in step 1 and phenol in step 2. MS (m/e): 346.3 (M−H⁻, 100%).

Example 32

2-(2-Methoxy-4-phenoxy-benzoylamino)-benzoic acid

In analogy to example 30, 2-(2-Methoxy-4-phenoxy-benzoylamino)-benzoic acid was prepared using 4-bromo-2-methoxy-benzoyl chloride [5213-16-1] in step 1 and phenol in step 2. MS (m/e): 346.3 (M−H⁻, 100%).

Example 33

5-Fluoro-2-(4-phenoxy-benzoylamino)-benzoic acid

In analogy to example 1,5-Fluoro-2-(4-phenoxy-benzoylamino)-benzoic acid was prepared form 2-amino-5-fluoro-benzoic acid and 4-phenoxy-benzoyl chloride [1623-95-6]. MS (m/e): 350.4 (M−H⁻, 100%).

Example 34

4-Fluoro-2-(4-phenoxy-benzoylamino)-benzoic acid

In analogy to example 1,4-Fluoro-2-(4-phenoxy-benzoylamino)-benzoic acid was prepared from 2-amino-4-fluorobenzoic acid and 4-phenoxy-benzoyl chloride [1623-95-6]. MS (m/e): 350.0 (M−H⁻, 100%).

Example 35

2-Fluoro-6-(4-phenoxy-benzoylamino)-benzoic acid

In analogy to example 1,2-Fluoro-6-(4-phenoxy-benzoylamino)-benzoic acid was prepared from 2-amino-6-fluoro-benzoic acid and 4-phenoxy-benzoyl chloride [1623-95-6]. MS (m/e): 350.1 (M−H⁻, 100%).

Example 36

2-[4-(3-Fluoro-phenoxy)-3-methyl-benzoylamino]-benzoic acid

Step 1

2-(4-Bromo-3-methyl-benzoylamino)-benzoic acid methyl ester

To 2-amino-benzoic acid methyl ester (3.1 g) in dichloromethane (31 mL) under slight cooling was added 3-methyl-4-bromobenzoyl chloride ([21900-25-4], 4.8 g) followed by a triethylamine (3.15 mL). The temperature of the solution was kept below 40° C. and the reaction mixture was then stirred at room temperature for an hour. After such time, additional dichloromethane was added (50 mL) and the reaction mixture was washed with water. The aqueous phase was further extracted with dichloromethane. The combined organic phases were dried over sodium sulfate and concentrated in vacuo. The residue was purified by column chromatography (heptane-ethyl acetate: 0-50%) to yield 2-(4-bromo-3-methyl-benzoylamino)-benzoic acid methyl ester (7.1 g). MS (m/e): 348.3 (M+H⁺, 100%).

Step 2

2-[4-(3-Fluoro-phenoxy)-3-methyl-benzoylamino]-benzoic acid

In analogy to example 2, 2-[4-(3-fluoro-phenoxy)-3-methyl-benzoylamino]-benzoic acid was prepared from 2-(4-bromo-3-methyl-benzoylamino)-benzoic acid methyl ester and 3-fluorophenol. MS (m/e): 364.0 (M−H⁻, 100%).

Example 37

2-[4-(2-Fluoro-phenoxy)-3-methyl-benzoylamino]-benzoic acid

In analogy to example 36, 2-[4-(2-fluoro-phenoxy)-3-methyl-benzoylamino]-benzoic acid was prepared from 2-(4-bromo-3-methyl-benzoylamino)-benzoic acid methyl ester and 2-fluorophenol. MS (m/e): 364.0 (M−H⁻, 100%).

Example 38

2-[4-(2,4-Difluoro-phenoxy)-3-methyl-benzoylamino]-benzoic acid

In analogy to example 36, 2-[4-(2,4-difluoro-phenoxy)-3-methyl-benzoylamino]-benzoic acid was prepared from 2-(4-bromo-3-methyl-benzoylamino)-benzoic acid methyl ester and 2,4-difluorophenol. MS (m/e): 382.0 (M−H⁻, 100%).

Example 39

4-Chloro-5-fluoro-2-(4-phenoxy-benzoylamino)-benzoic acid

Step 1

N,N-di-tert-Butyloxycarbonyl-2-bromo-5-chloro-4-fluoro-aniline

This compound was prepared in analogy to the method of Darnbrough et al. (*Synth. Comm.* 2001, 31, 3273): Under an atmosphere of Nitrogen, di-tert-butyl dicarbonate [24424-99-5], 8.839 g) was added to a cooled (0° C.) solution of 2-bromo-5-chloro-4-fluoro-aniline ([85462-59-5], 3.03 g) and DMAP (0.165 g) in THF (20 ml). After 4 h at r.t., the reaction mixture was taken up in ethyl acetate, washed with 1N HCl and brine, and dried (Na₂SO₄). The solvent was evaporated and the residue purified by column chromatography (silica gel, n-heptane, ethyl acetate) to give the title compound (4.66 g, 81%). ¹H NMR (CDCl₃): δ 1.42 (s, 18H), 7.28 (d, 1H), 7.42 (d, 1H).

Step 2

2-tert-Butyloxycarbonylamino-4-chloro-5-fluoro-benzoic acid tert-butyl ester

This compound was prepared in analogy to the method of Herzig et al. (*Synlett* 2005, 3107): Under an atmosphere of Nitrogen, a solution of n-butyl lithium in hexane (1.6N, 3.72 ml) was added dropwise at a temperature of −78° C. to a solution of N,N-di-tert-butyloxycarbonyl-2-bromo-5-chloro-4-fluoro-aniline (2.3 g) in THF (10 ml). After 30 min, the mixture was allowed to warm to r.t., then quenched with satd. NH₄Cl, and extracted with ethyl acetate. The extract was dried (Na₂SO₄) and evaporated. The residue was purified by column chromatography (silica gel, n-heptane, ethyl acetate) to give the title compound (0.68 g, 36%). ¹H NMR (CDCl₃): δ 1.42 (s, 9H), 1.60 (s, 9H), 7.70 (d, 1H), 8.62 (d, 1H), 10.25 (bs, 1H).

Step 3

4-Chloro-5-fluoro-2-(4-phenoxy-benzoylamino)-benzoic acid

Under an atmosphere of Argon, 2-tert-butoxycarbonylamino-4-chloro-5-fluoro-benzoic acid tert-butyl ester (200 mg) and 4-phenoxy-benzoyl chloride ([1623-95-6], 269 mg) were dissolved in THF (5 mL). Triethylamine (0.24 ml) was added, and the mixture was heated to reflux overnight. The solvent was evaporated, and the residue was purified by column chromatography (silica gel/methanol/dichloromethane). The eluate, which contained two UV-absorbing components, was evaporated, and the residue was dissolved in a mixture of dichloromethane (0.5 ml) and trifluoroacetic acid (0.5 ml). After 2 h, the volatiles were evaporated, and the title compound (9 mg, 0.4%) was isolated from the mixture by preparative, reversed-phase HPLC (Agilent Zorbax XdB C18 column, solvent gradient 5-95% CH₃CN in 0.1% TFA(aq) over 4.5 min, flow rate 30 ml/min). MS: m/e=384.1 [M+H⁺].

Example 40

2-(4-Phenoxy-benzoylamino)-5-trifluoromethyl-benzoic acid

In analogy to example 39, 2-(4-phenoxy-benzoylamino)-5-trifluoromethyl-benzoic acid was prepared from 2-bromo- 4-trifluoromethyl-phenylamine (57946-63-1). $^1$H NMR (d$^6$-DMSO): δ 7.14-7.18 (4H, m), 7.25-7.28 (1H, m), 7.45-7.50 (2H, m), 8.00-8.02 (2H, m), 8.04-8.05 (1H, m), 8.28-8.29 (1H, m), 8.90-8.92 (1H, m), 12.33 (1H, bs), 14.40 (1H, bs).

Example 41

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example 42

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 43

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example 44

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 45

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound selected from the group consisting of:
2-(4-Benzyloxy-benzoylamino)-benzoic acid,
2-[4-(4-Fluoro-phenoxy)-benzoylamino]-benzoic acid,
2-[4-(3,4-Dichloro-phenoxy)-benzoylamino]-benzoic acid,
2-(4-p-Tolyloxy-benzoylamino)-benzoic acid,
2-[4-(3-Methoxy-phenoxy)-benzoylamino]-benzoic acid,
2-(4-o-Tolyloxy-benzoylamino)-benzoic acid,
2-[4-(4-Methoxy-phenoxy)-benzoylamino]-benzoic acid,
2-[4-(4-Chloro-phenoxy)-benzoylamino]-benzoic acid,
2-[4-(3,4-Difluoro-phenoxy)-benzoylamino]-benzoic acid,
2-[4-(4-Methanesulfonyl-phenoxy)-benzoylamino]-benzoic acid, 2-{4-[4-Methoxycarbonyl)phenoxy]benzoyl}aminobenzoic acid,
2-[4-(3,5-Dichloro-phenoxy)-benzoylamino]-benzoic acid,
2-[4-(4-Cyano-phenoxy)-benzoylamino]-benzoic acid,
2-[4-(2-Fluoro-phenoxy)-benzoylamino]-benzoic acid,
2-[4-(2-Chloro-phenoxy)-benzoylamino]-benzoic acid,
2-[4-(3-Fluoro-phenoxy)-benzoylamino]-benzoic acid,
2-[4-(3-Chloro-phenoxy)-benzoylamino]-benzoic acid,
2-(4-m-Tolyloxy-benzoylamino)-benzoic acid,
2-[4-(Quinolin-8-yloxy)-benzoylamino]-benzoic acid,
2-[4-(4-Trifluoromethyl-phenoxy)-benzoylamino]-benzoic acid,
2-[4-(4-Carbamoyl-phenoxy)-benzoylamino]-benzoic acid,
2-[4-(4-Dimethylaminomethyl-phenoxy)-benzoylamino]-benzoic acid,
2-[4-(4-[1,2,4]Triazol-1-yl-phenoxy)-benzoylamino]-benzoic acid,
2-[4-(2,4-Difluoro-phenoxy)-benzoylamino]-benzoic acid,
2-[4-(Pyridin-2-yloxy)-benzoylamino]-benzoic acid,
2-[4-(Pyridin-3-yloxy)-benzoylamino]-benzoic acid,
2-[4-(3,4-Dimethyl-phenoxy)-benzoylamino]-benzoic acid,
2-[4-(2,3-Difluoro-phenoxy)-benzoylamino]-benzoic acid,
2-[4-(2,5-Difluoro-phenoxy)-benzoylamino]-benzoic acid,
2-(3-Methyl-4-phenoxy-benzoylamino)-benzoic acid,
2-(2-Methyl-4-phenoxy-benzoylamino)-benzoic acid,
2-(2-Methoxy-4-phenoxy-benzoylamino)-benzoic acid,
5-Fluoro-2-(4-phenoxy-benzoylamino)-benzoic acid,
4-Fluoro-2-(4-phenoxy-benzoylamino)-benzoic acid, and
2-Fluoro-6-(4-phenoxy-benzoylamino)-benzoic acid,
2-[4-(3-Fluoro-phenoxy)-3-methyl-benzoylamino]-benzoic acid,
2-[4-(2-Fluoro-phenoxy)-3-methyl-benzoylamino]-benzoic acid,
2-[4-(2,4-Difluoro-phenoxy)-3-methyl-benzoylamino]-benzoic acid,
4-Chloro-5-fluoro-2-(4-phenoxy-benzoylamino)-benzoic acid, and
2-(4-Phenoxy-benzoylamino)-5-trifluoromethyl-benzoic acid,
or pharmaceutically acceptble salts and esters thereof.

2. The compound according to claim 1, selected from the group consisting of
2-(4-o-Tolyloxy-benzoylamino)-benzoic acid,
2-[4-(2-Fluoro-phenoxy)-benzoylamino]-benzoic acid,
2-[4-(2-Chloro-phenoxy)-benzoylamino]-benzoic acid,
2-[4-(3-Fluoro-phenoxy)-benzoylamino]-benzoic acid,
2-(4-m-Tolyloxy-benzoylamino)-benzoic acid,
2-[4-(Quinolin-8-yloxy)-benzoylamino]-benzoic acid,
2-[4-(4-[1,2,4]Triazol-1-yl-phenoxy)-benzoylamino]-benzoic acid,
2-[4-(2,4-Difluoro-phenoxy)-benzoylamino]-benzoic acid,
2-[4-(Pyridin-2-yloxy)-benzoylamino]-benzoic acid,
2-[4-(2,5-Difluoro-phenoxy)-benzoylamino]-benzoic acid,
2-(3-Methyl-4-phenoxy-benzoylamino)-benzoic acid,
4-Fluoro-2-(4-phenoxy-benzoylamino)-benzoic acid, and
2-Fluoro-6-(4-phenoxy-benzoylamino)-benzoic acid
or pharmaceutically acceptable salts and esters thereof.

* * * * *